(12) United States Patent
Jenkins et al.

(10) Patent No.: US 7,866,223 B2
(45) Date of Patent: Jan. 11, 2011

(54) METHOD OF OBTAINING SAMPLES OF MEAT TO ASSAY FOR MICROBIAL CONTAMINATION

(75) Inventors: Sherri Jenkins, Pierce, CO (US); Scott Leach, Greeley, CO (US); Art Rogers, Greeley, CO (US)

(73) Assignee: Swift & Company, Greeley, CO (US)

( * ) Notice: Subject to any disclaimer, the term of this patent is extended or adjusted under 35 U.S.C. 154(b) by 8 days.

(21) Appl. No.: 11/757,812

(22) Filed: Jun. 4, 2007

(65) Prior Publication Data

US 2008/0295619 A1     Dec. 4, 2008

(51) Int. Cl.
*G01N 1/04*     (2006.01)
*B23B 45/02*    (2006.01)

(52) U.S. Cl. ............ 73/864.44; 73/864.43; 408/204
(58) Field of Classification Search ........... 73/863, 73/864.41–864.45, 864.51, 864.91; 408/204, 408/205, 207
See application file for complete search history.

(56) References Cited

U.S. PATENT DOCUMENTS

| | | | |
|---|---|---|---|
| 2,525,604 A * | 10/1950 | Johnson ................ 452/10 |
| 2,987,922 A * | 6/1961 | Harrington ............ 73/864.44 |
| 3,683,892 A * | 8/1972 | Harris .................. 600/567 |
| 3,936,934 A | 2/1976 | Bowden |
| 3,947,920 A | 4/1976 | Voornas |
| 4,046,046 A | 9/1977 | Pearson et al. |
| 4,136,447 A | 1/1979 | Gillham, Sr. |
| 4,149,414 A * | 4/1979 | Walker ................. 73/864.43 |
| 4,300,286 A | 11/1981 | Panchula |
| 4,310,969 A | 1/1982 | Cannizzaro et al. |
| 4,534,229 A * | 8/1985 | Funk et al. ............. 73/863 |
| 4,590,377 A | 5/1986 | Lukens |
| 4,640,187 A | 2/1987 | Wallick et al. |
| 4,643,019 A | 2/1987 | Jones |
| 4,763,414 A | 8/1988 | McNeill, II |
| 5,005,433 A * | 4/1991 | Patton ................. 73/864.44 |
| 5,056,223 A | 10/1991 | Buck et al. |
| 5,114,399 A | 5/1992 | Kovalcheck |
| 5,133,688 A | 7/1992 | Hutchinson |
| 5,234,372 A | 8/1993 | Hutchinson |
| 5,324,300 A | 6/1994 | Elias et al. |

(Continued)

FOREIGN PATENT DOCUMENTS

WO     WO 00/57153 A1 *    9/2000

OTHER PUBLICATIONS

"Burnishing Tools and Machines" to Cogsdill Tool Products, 2002, pp. 1-57.*

(Continued)

*Primary Examiner*—David A. Rogers
(74) *Attorney, Agent, or Firm*—Sheridan Ross P.C.

(57) ABSTRACT

The present invention generally relates to a device for obtaining samples of meat during commercial meat production. More specifically, embodiments of the present invention provide for an automated, hand held device used to rapidly obtain samples of meat that are of essentially uniform size in order to test for the presence of microbiological contaminants in such meat, as well as methods of using the device. The device can be used to comply with laws and regulations concerning the testing of meat for microbial contamination during commercial meat production. The device is also lightweight and ergonomically constructed so that it may be operated by a single individual.

18 Claims, 2 Drawing Sheets

U.S. PATENT DOCUMENTS

| | | | |
|---|---|---|---|
| 5,433,121 | A | 7/1995 | Torra et al. |
| 5,590,591 | A | 1/1997 | Kim |
| 5,670,162 | A | 9/1997 | Baile et al. |
| 5,672,357 | A | 9/1997 | Baile et al. |
| 5,697,935 | A | 12/1997 | Moran et al. |
| 5,794,344 | A | 8/1998 | Poulos et al. |
| 5,852,875 | A | 12/1998 | Dolah |
| 5,865,259 | A | 2/1999 | Catto |
| 5,897,561 | A | 4/1999 | Raines |
| 5,947,989 | A | 9/1999 | Shikhman et al. |
| 5,954,671 | A | 9/1999 | O'Neill |
| 5,980,545 | A | 11/1999 | Pacala et al. |
| 6,032,368 | A | 3/2000 | Huang et al. |
| 6,120,367 | A | 9/2000 | Scott et al. |
| 6,148,719 | A | 11/2000 | Poltielov |
| 6,440,373 | B1 | 8/2002 | Gomes et al. |
| 6,494,844 | B1 | 12/2002 | Van Bladel et al. |
| 6,716,464 | B1 | 4/2004 | Schlegel et al. |
| 6,769,186 | B1 | 8/2004 | Sakhleh et al. |
| 6,945,942 | B2 | 9/2005 | Van Bladel et al. |
| 6,959,617 | B2 | 11/2005 | Deppermann |
| 7,020,968 | B1 | 4/2006 | Abdel-Dayem |
| 7,029,387 | B2 | 4/2006 | van den Nieuwelaar et al. |
| 7,059,207 | B2 * | 6/2006 | Harris ............ 73/864.45 |
| 7,093,481 | B2 * | 8/2006 | Morris ............ 73/61.62 |
| 7,121,356 | B2 | 10/2006 | Michael |
| 2003/0037440 | A1 | 2/2003 | Raz |
| 2005/0044971 | A1 * | 3/2005 | Harris ............ 73/864.43 |
| 2005/0066751 | A1 * | 3/2005 | Harris ............ 73/864.45 |
| 2006/0266131 | A1 * | 11/2006 | Graham ............ 73/864.44 |
| 2007/0213755 | A1 * | 9/2007 | Beckman et al. ........ 606/170 |
| 2007/0215736 | A1 * | 9/2007 | Young et al. .......... 241/292.1 |
| 2008/0102442 | A1 * | 5/2008 | Samadpour ............ 435/4 |

OTHER PUBLICATIONS

Eustace et al., "Sampling Boneless Meat for Chemical Lean Measurement", Proceedings of a Meat Quality Control Workshop, Oct. 1988, pp. 106-125.*

"A Corer for Sampling of Chilled Boneless Cartoned Meat", CSIRO Meat Research Newsletter, Jul. 1971.*

"Sampling of Cartoned Meat and Preparation for Chemical Lean Determination", Meat Research Corporation, 1997.*

"Fat Analysis", CSIRO Meat Research Newsletter, Jul. 1972.*

International Search Report for International (PCT) Patent Application No. PCT/US07/70439, mailed Dec. 13, 2007.

Written Opinion for International (PCT) Patent Application No. PCT/US07/70439, mailed Dec. 13, 2007.

K.W. McMillin, "Novel purge collection system for microbiological analyses of meat", abstract from 2003 Institute of Food Technologists Annual Meeting in Chicago, available at http://ift.confex.com/ift/2003/techprogram/paper_20683.htm, pp. 1-2.

J.A. Scanga et al., "A Microbiological Profile of Domestic and Imported Beef Raw Materials Destined for Use in Ground Beef Production", CSU Beef Program Report, available at http://ansci.colostate.edu/files/meat_science/scanga.pdf, 1999, pp. 177-182.

Tommy L. Wheeler et al., "Warner-Brazler Shear Force Protocol", USDA-ARS U.S. Meat Animal Research Center, presentation, available at http://www.ars.usda.gov/SP2UserFiles/Place/54380530/protocols/WBSProtocol.pdf, pp. 1-15.

Des E. Bailey and Ian J. Eustace, "The Air Ejection Corer for Sampling Chilled Boneless Cartoned Meat", Meat Research Report Jan. 1989, Commonwealth Scientific and Industrial Research Organization (Australia), available at http://www.meatupdate.csiro.au/data/MEAT_RESEARCH_REPORT_01-89.pdf, May 1989, pp. 1-8.

International Preliminary Report on Patentability for International (PCT) Patent Application No. PCT/US07/70439, mailed Dec. 17, 2009.

* cited by examiner

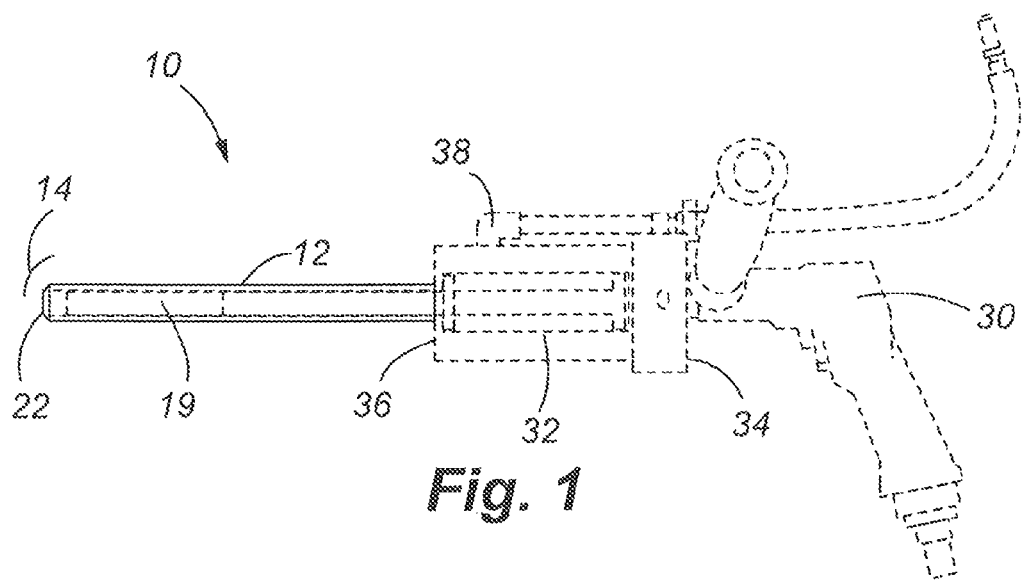
Fig. 1
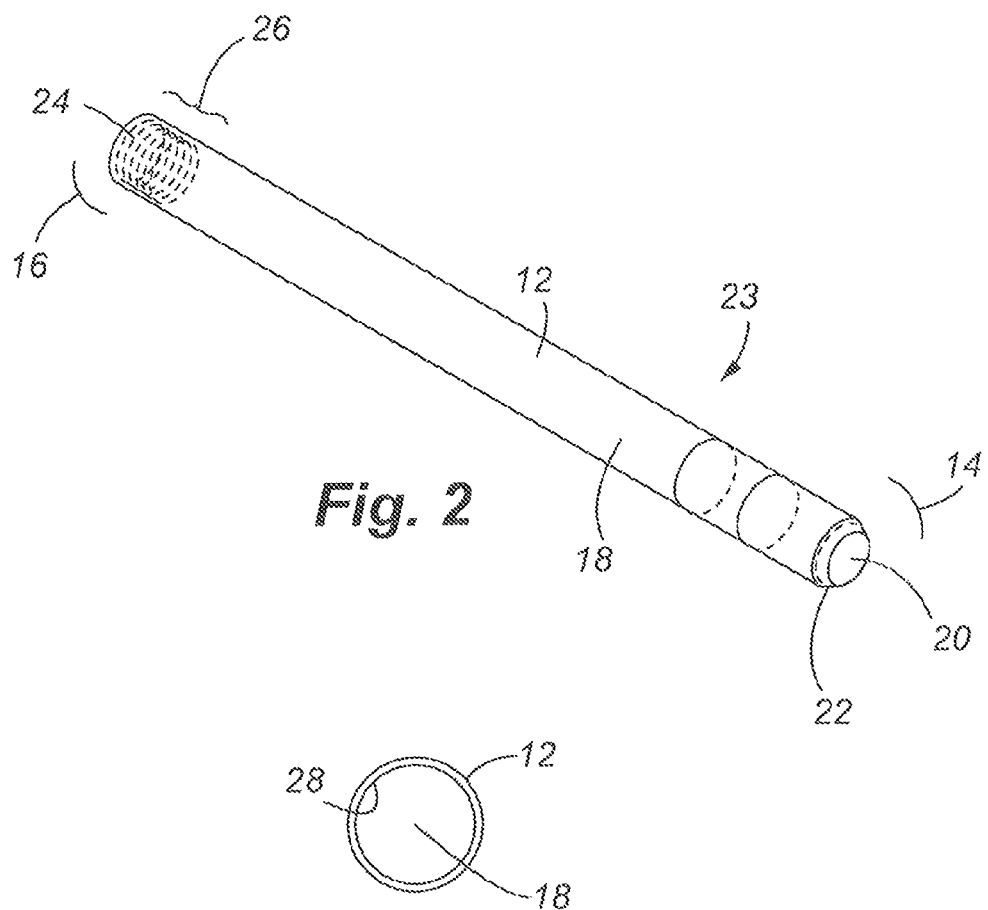
Fig. 2
Fig. 3

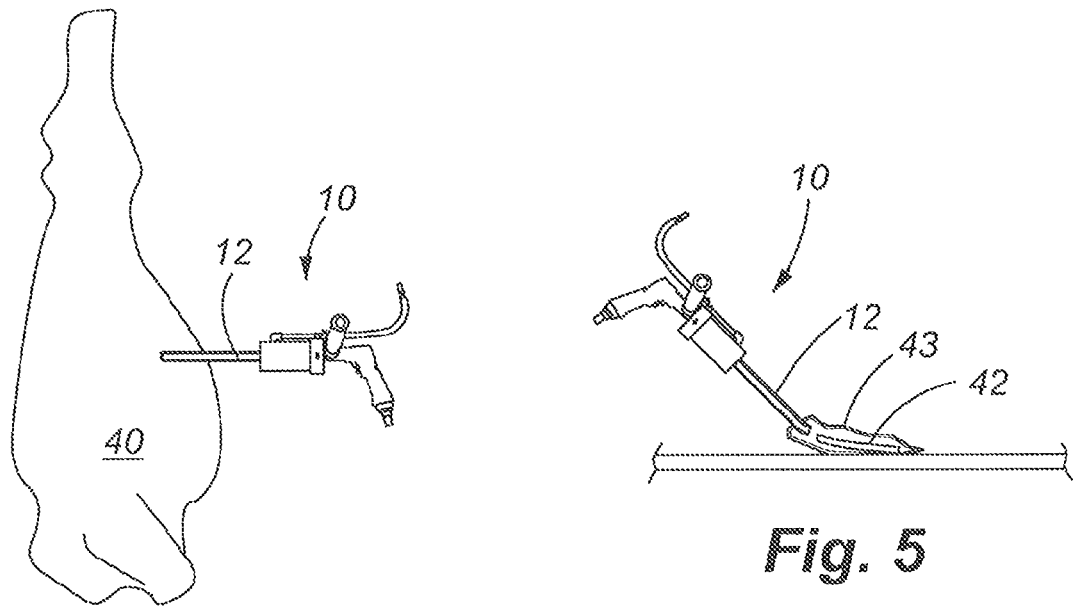
Fig. 4A
Fig. 5
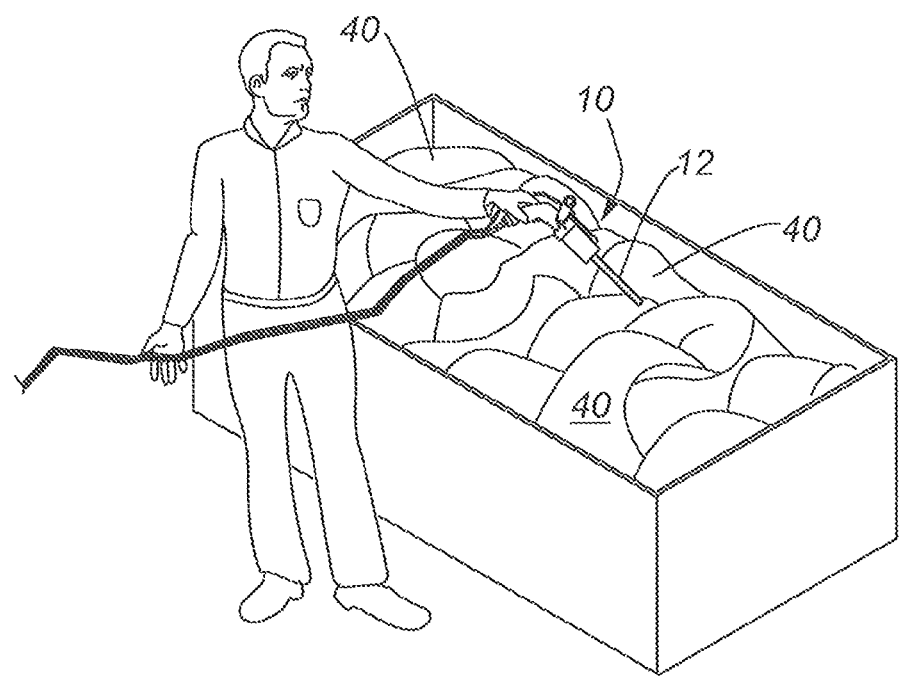
Fig. 4B

METHOD OF OBTAINING SAMPLES OF MEAT TO ASSAY FOR MICROBIAL CONTAMINATION

FIELD OF THE INVENTION

The present invention generally relates to a device for obtaining samples of meat during commercial meat production. More specifically, embodiments of the present invention provide for an automated, hand held device used to rapidly obtain samples of meat that are of essentially uniform size in order to test for the presence of microbiological contaminants in such meat, as well as methods of using the device.

BACKGROUND OF THE INVENTION

Commercial meat processing plants and slaughter houses go to great lengths to reduce or eliminate, to the extent possible, the threat of bacterial or microbial contamination in their production facilities and, more importantly, in their meat products. The safe and clean handling and processing of meat is an essential step toward the prevention of those food borne illnesses that result when meat is contaminated with pathogenic microbes such as *Clostridium botulinum, Campylobacter, Escherichia coli, Listeria monocytogenes, Salmonella*, and others, and the U.S. government has established several laws directed toward this very purpose, such as Chapter 12 of the Federal Meat Inspection Act (21 U.S.C. 601, et seq.), and several regulations have been promulgated by the U.S. Department of Agriculture pursuant to these laws that govern the proper handling and processing of meat, such as Part 300 et seq. of Title 9 of the Code of Federal Regulations. Meat processing plants must regularly test the meat located within their production facilities for the presence of such microbes in order to remain compliant with these laws and regulations. Testing is done at several points along the production line, as well as at the packaging station, in order to ensure that the meat remains clean and uncontaminated throughout the production process. As may be expected, in order to comply with such laws and regulations, such testing must be performed pursuant to exacting governmental standards, which include strict guidelines as to the size of each sample of meat to be tested.

Several methods have been implemented to comply with these laws and regulations. Presently, meat processing plants station large bins at a plurality of locations along the production line, which are used to collect the trimmings from the meat then in production. These bins are large enough to hold approximately 2,000 pounds of trimmings, subprimal cuts (e.g. consumer cuts, retail cuts, or market ready cuts), or extra fat beef trimmings, all of which must be tested for the presence of microbial contaminants before they are packaged or sold. As can be appreciated, if the test results reveal the presence or absence of any microbial contaminant in a single bin, those results can be used to infer the presence or absence of that contaminant at the station of the processing plant where the bin is located. In order to obtain a sample of meat from the meat trimmings in such bins, a production facility employee will typically use a hook to remove a single piece of meat from a bin and then use a knife to cut a portion from the trimming, of the proper size and shape for testing, as aseptically as possible. Thereafter, the employee will transfer the cut sample into a plastic collecting bag and send it to be tested. Several series of tests are typically run from a single bin, each necessitating the talking of a sample, and each bin in the production facility must be tested at regular, recurring timed intervals. Therefore, the employee will have to perform the task of sampling numerous times at each bin, often several times per week, and it is common for the employee to hurry through the large number of samples in order to complete the task in a timely manner. Since each sample is cut by hand, there is little to no uniformity of size to the samples collected. Because the laws and regulations require testing of samples of a very specific size, it is often necessary to cut the samples again to the size and shape needed for proper testing.

In addition to the foregoing troubles, the risk of cross contamination is omnipresent with this traditional method, as the employee may pick up a contaminated trimming in one location of the meat processing plant and through human error or haste, transfer the contaminant to a different bin at a different location, thereby yielding a false result for the presence of a microbial pathogen in the second bin. It is also possible that the employee will contaminate a trimming directly through human contact with the sample, which will yield a false positive for an otherwise uncontaminated bin. These troubles beget yet another problem with this method in that the employees taking these samples are made aware of the risk of cross contamination and, to avoid human contact with the trimmings in the bin and thus cross-contamination, they compensate by removing and testing only those trimmings at the top of the bin, leaving the balance untested. The manual sampling task is therefore arduous, difficult, time consuming, variable and often dependent upon the vicissitudes of the operator.

In an attempt to overcome some of the foregoing difficulties, several devices have been created that are designed to obtain meat samples for various uses. One such device is a hand-held drill bit which includes a two-part rotating tubular blade threaded onto the chuck of the drill, such as that manufactured and sold by J&B Haig Products of Queensland, Australia. The blade of this drill bit has a fixed, non-scalable or adjustable, 22 millimeter internal diameter and is manufactured in two parts which must be threaded together to form the functional sampling bit, which is then threaded onto the chuck of a hand-held drill. The first part of the bit is a hollow, tubular metal carbide blade used to cut into the meat of interest that is threaded onto the second part of the bit, which is a non-carbide metal connecting tube used to connect both parts to a hand-held power drill. In operation, the device is used to drill the bladed tip into the meat of interest in order to remove a sample, which is then removed from the meat and ejected from the cylindrical blade. This device suffers from varying practical deficiencies including, most notably, the fact that it was not manufactured to help meat processing plants comply with the laws and regulations described above. Additionally, the bit is manufactured in two separate pieces, with each piece being made of a different material. Therefore, differences in the materials and the casting process can lead to variations in thickness between the two parts such that when the bladed tip and the connecting tube are threaded together they create structures, such as lips and recesses, at the point of threaded connection where meat, and thus microbial contaminants if they are present, may become embedded. This makes the two-part tube quite difficult to clean and sanitize, thereby perpetuating the risks of cross contamination described above. The sample size obtained from this device is too small for proper testing under U.S. law as the internal bore of the tubular blade does not yield a sample of sufficient size for testing. Additionally, because of the narrow internal diameter, the collected samples often become pulverized upon ejection from the device, which makes testing impossible as the samples need to be intact to comply with the foregoing laws and regulations. Other devices typically used to obtain samples of meat for varying purposes, such as those typically referred to in the commercial meat production industry as the "six-shooter" and the "single-shooter," are large, bulky devices that were designed for a completely different purpose are thus not capable of being operated by a single user. These devices are typically used to sample meat and test for fat content, which necessitates the removal of very large samples inappropriate for use in microbial testing.

SUMMARY

The present invention overcomes the foregoing deficiencies and may be used by meat producers to quickly and easily comply with Chapter 12 of the Federal Meat Inspection Act (21 U.S.C. 601, et seq.), Part 300 et seq. of Title 9 of the Code of Federal Regulations, and other laws and regulations relating to the sampling and testing of meat during commercial meat production that currently exist and that may be promulgated from time to time. The advantages offered by the present invention may be realized in the production of meat products from all types of commercially useful livestock where the testing for microbial contaminants is mandatory, such as bovine, porcine and ovine species, as well as bison, poultry and fish. Methods of using the device of the present invention to comply with such laws and regulations are also presented.

In accordance with one embodiment of the present invention, a device for obtaining one or more essentially uniform samples of meat is provided. The device comprises an elongated hollow member with a first open end, a second open end oriented opposite to the first open end, and an internal cavity extending the entire length of the hollow member. The first open end defines a first opening in the hollow member and has a cutting surface. The second open end defines a second opening in the hollow member and includes a coupling mechanism disposed on the interior surface of the hollow member, which initiates at the second opening at the second open end and extends along the interior surface of the hollow member at least partially into the internal cavity. The device also has a driving means that applies rotational motion to the hollow member, which is adapted to be driven into and through, via the rotational motion, at least one piece of meat, and preferably a plurality of meat pieces, thereby producing at least one sample of the piece(s) of meat which becomes disposed in the internal cavity. The hollow member of the device is also adapted to be removed from the piece, or pieces, of meat with the sample(s) remaining disposed in the internal cavity so that the sample(s) may be expelled from the internal cavity of the device via the expulsion means described in detail hereinbelow.

In accordance with another embodiment of the present invention, a method of using the device to obtain one or more essentially uniform samples of meat is provided. The method comprises the first step of separating at least one piece, and preferably a plurality of pieces, of meat of interest from an animal and placing those samples into a storage container, such as a bin capable of holding 2,000 pounds of meat pieces. Next, a sampling device made in accordance with at least one embodiment of the present invention is driven into and through the piece, or pieces, of meat so that a sample of the piece, or pieces, of meat becomes disposed within the interior of the sampling device. The sampling device is then removed from the piece(s) of meat with the sample(s) of the piece(s) of meat remaining disposed in the interior of the sampling device. Thereafter, the sample(s) are expelled from the device into a means of collecting the sample(s) in advance of testing for the presence of microbial contamination.

Yet another aspect of the present invention is to provide a device that will allow meat producers to quickly and easily comply with the laws and governmental regulations regarding the sampling and testing of their meat and meat products for microbial contamination which is readily scalable and therefore can be easily updated and expanded to comply with new government regulations as they are promulgated. In that regard, as new laws are passed and regulations issued, and as existing laws and regulations are modified, which introduce new requirements for the sampling and testing of meat products, meat producers will be able to modify and adapt the present invention in such a way so as to remain compliant with those new and modified laws and regulations without incurring large costs. Therefore, embodiments of the present invention provide for a relatively easily scalable device.

Another aspect of the present invention is directed to a method for obtaining samples of meat in a fashion that substantially reduces the opportunity for microbial contamination of such samples. Such method includes obtaining a substantially uniform meat sample within an internal hollow core of a sampling device, expelling the meat contained within the hollow core and finally assaying the collected meat sample for microbial contamination. The coring element can rotate or otherwise move (e.g., via motorized elements) to assist in the sampling procedure and/or the expelling step. In certain embodiments, the coring device element that actually contacts the meat and travels through at least one piece of meat, is of a uniform and integral construction, such that the hollow coring element is of one consistent length and interior dimension. In other embodiments however, variations in the diameter (either interior or exterior) of the hollow coring element can be made, for example, to provide a slightly elongated cone or slanted sidewalls in order to facilitate desired ease of conducting the element through meat and/or in expelling meat core elements from the device. The coring element can rotate or otherwise move (e.g., via motorized elements) to assist in the sampling procedure and/or the expelling step. In certain embodiments, meat collected within the hollow interior is expelled through the same end as is first contacted with meat samples contained within a bin. In other embodiments, however, meat may be expelled in the reverse direction. In these embodiments, a motorized attachment to the hollow core element is detachable from the hollow core element so that meat products can be expelled from the end of the hollow core that attaches to the motorized element.

In still other embodiments, however, the hollow core element is made from more than one element/piece of material. In such embodiments, the connection or coupling of two or more hollow core elements is adapted such that contamination with undesired microorganisms is reduced or prohibited. Such couplings may involve, for example, bayonet mounts, screw mounts, etc. The provision of a hollow core element having more than one portion provides the ability of an operator to adjust the length of the hollow core element for particular situations and applications. It is therefore within one aspect of the present invention to provide variably sized lengths and/or diameters of hollow core elements that may be operatively associated with each other to provide desired lengths and/or other configurations for particular coring operations. Such elements may, in some embodiments be flexible, rather than rigid, to accommodate particular uses/situations. They may also be made of disposable material, thus further reducing the opportunity for contamination.

Another aspect of the present invention relates to the adjustability of the diameter of a cored meat sample obtainable from a particular hollow cored element. For example, one meat contacting end of the hollow core element may be adjustable such that a cutting edge that contacts the meat is either larger than and/or less than the remaining diameter of the hollow core element, thus facilitating expelling procedures.

In still other embodiments of the present invention, the hollow core element itself is made of more than one type of material, with at least one type of material being flexible and adaptable to being bent in various configurations. For example, in one embodiment, a meat contacting cutting element is provided in association with a flexible plastic hollow tube. The hollow tube can be, in some embodiments, disposable, and/or can be fitted with a plastic film material on its innermost circumference in order to provide for meat samples to be not only separated from meat pieces within a container bin, but when extracted from such meat container bin, can be immediately packaged in a relatively sterile film coating to thereafter permit relatively easy extraction, storage and to facilitate further analysis of such separated meat, without undue risk of contamination. In certain embodiments, a telescoping relationship of a plurality of hollow core tubes can be employed, which one of ordinary skill in the art will appreciate how best to construct in any particular embodiment/situation.

In another embodiment, a plunger-type mechanism is operatively associated with the hollow coring element such that cored meat samples can be expelled from the hollow core center by operation of the plunger to void the collected meat samples from the hollow element(s).

An automated system employing one or more coring devices of the present invention can be employed by providing machines that are programmed to locate meat containing bins, direct one or more hollow cored elements into particular predetermined positions within the meat container bins and at predetermined depths, extract meat pieces within the hollow core elements, remove and/or lift the hollow core elements containing meat samples from particular bin contains, and expel collected meat from the hollow core elements in a manner that precludes substantial microbial contamination and/or human contact with such meat samples.

These and other advantages will be apparent from the disclosure of the invention(s) contained herein. The above-described embodiments and configurations are neither complete nor exhaustive. As will be appreciated, other embodiments of the invention(s) are possible using, alone or in combination, one or more of the features set forth above or described in detail below.

It should be understood that this summary of the invention does not necessarily describe each and every aspect of the present invention. One of ordinary skill in the art will understand the scope and nature of the claimed invention through a review of the entire specification, the claims and, within common sense principles and ordinary creativity of one of ordinary skill in the art, will understand that all such modifications or developments to the present invention are intended to and shall be construed as being disclosed and incorporated herein.

BRIEF DESCRIPTION OF THE DRAWINGS

FIG. 1 is a perspective view of a sampling device attached to certain driving means and certain expelling means in accordance with at least some embodiments of the present invention;

FIG. 2 is a close-up perspective view of the sampling device depicted in FIG. 1 in accordance with at least some embodiments of the present invention;

FIG. 3 is an end-view perspective view of the sampling device depicted in FIG. 2 in accordance with at least some embodiments of the present invention;

FIG. 4A is a perspective view of a sampling device in operation that is attached to certain driving means and certain expelling means that is in use in accordance with at least some embodiments of the present invention;

FIG. 4B is another perspective diagram of a sampling device in operation that is attached to certain driving means and certain expelling means that is in use in accordance with at least some embodiments of the present invention; and FIG. 5 is a diagram of a sampling device expelling a sample of collected meat.

DETAILED DESCRIPTION OF A PREFERRED EMBODIMENT

Referring initially to FIGS. 1, 2 and 3, a device 10 for obtaining one or more essentially uniform samples of meat according to at least some embodiments of the present invention is provided. The device 10 is comprised of an elongated hollow member 12 with a first open end 14, a second open end 16 oriented opposite to the first open end, and an internal cavity 18 extending the length of the hollow member 12. The first open end 14 defines a first opening 20 in the hollow member which includes a cutting surface 22. The second open end 16 defines a second opening 24 in the hollow member and includes a coupling mechanism 26 disposed on the interior surface 28 of the hollow member 12 at the second open end 16. The coupling mechanism 26 extends along the interior surface 28 of the hollow member 12 at least partially into the internal cavity 18. The device 10 also includes a driving means 30 that applies rotational motion to the hollow member 12. The hollow member 12 is adapted to be driven, via rotational motion provided by the driving means 30, into at least one piece of meat, and preferably a plurality of meat pieces, thereby producing a sample of the piece, or pieces, of meat which become(s) disposed in the internal cavity 18. In some embodiments, the hollow member 12 is adapted to be driven into and through at least one piece of meat, and preferably a plurality of meat pieces. The hollow member 12 of the device 10 is also adapted to be removed from the piece, or pieces, of meat with the sample(s) remaining disposed in the internal cavity 18, so that the sample(s) may be expelled from the internal cavity 18 of the device 10 at some distance away from the pieces of meat, via an expulsion means described further herein.

In some embodiments, the elongated hollow member 12 is a single article of unitary construction that can be made out of any metal capable of being sharpened and/or having a cutting edge 22, such as steel, iron, carbide, or aluminum, but may also be made of other materials capable of achieving a cutting edge 22 that is sufficiently sharp for purposes of the present invention, such as obsidian, glass, titanium, ceramic, plastic, or similar materials. In the presently preferred embodiment, the elongated hollow member 12 is made of stainless steel, or a similar type of steel with a high alloy content (e.g. approximately 12-18% chromium, titanium, cobalt or similar additions), is more preferably the stainless steel alloy of 17-4 PH precipitation hardened, martensitic stainless steel, with copper and niobium/colombium additions, and is even more preferably grade 420 stainless steel. It is also preferable that the hollow member 12 be cast as a single article and heat treated after casting in order to increase the hardness of the steel, thereby making the cutting surface 22 of the first open end 14 of the hollow member 12 easier to sharpen and enhancing its ability to maintain sharpness.

The hollow member 12 may be cast in any number of shapes that will serve to remove one or more samples of meat from a plurality of meat trimmings that are of sufficient size and shape for microbial testing pursuant to the foregoing laws and regulations. It is preferable, however, that the hollow member 12 be cast as an elongated hollow cylinder or tube, with the first open end 20 and the second open end 24 being circular in shape.

In another embodiment, the elongated hollow member 12 is made from a blend of metals, such that the first open end 14 of the hollow member 12 is made of a softer metal or stainless steel alloy that is easier to sharpen and reshape so that the cutting edge 22 may be properly maintained, and the second open end 16 of the hollow member 12 is made of a harder metal or stainless steel alloy that will maintain the shape and integrity of the hollow member 12 over time as it is used. In this embodiment the hollow member 12 is cast as a single article out of the two metals of interest, with the most terminal portion of each open end 14 and 16 being purely the softer metal or the harder metal, respectively, and the balance of the hollow member 12 being a blend of the two metals such that a gradient of the softer metal or stainless steel alloy is created that goes from an area of highest or pure concentration at the first open end 14 to an area of low to non-existing, concentration at the second open end 16. A similar gradient would thus be established for the harder metal or stainless steel alloy with the area of high concentration located at the second open end 16.

It is an object of the present invention that the device 10 be operable to obtain samples that are of optimal size and shape for microbial testing pursuant to existing laws and regulations. In that regard, the size, length and diameter of the hollow member 12 must be properly configured to comply with such laws and regulations so that it can create samples of the proper size and remove them from the meat to be tested. It is also an object of the present invention for the hollow member 12 to be sufficiently scalable such that its size, length and diameter can be made larger or smaller to comply with the laws and regulations governing the sampling and testing of meat as they change and with new laws and regulations that may be promulgated from time to time. In the presently preferred embodiment, the length of the hollow member 12 preferably ranges from 8 to 16 inches in length and is even more preferably 12 inches in length, and the diameter of the hollow member 12 preferably ranges from 0.5 to 3 inches in diameter, and is even more preferably 1 inch in diameter. The hollow member 12 of the present invention is therefore sized so that it can obtain samples from one, or from a plurality, of meat pieces that are of the proper size and shape for testing pursuant to such laws and regulations without damaging the samples in any way and so that the samples that are obtained can be expelled from the internal cavity 18 of the hollow member 12 intact. This confers a substantial advantage over many known devices which contain inner diameters that are so narrow they pulverize the meat samples either as they are obtained, or as they are expelled.

It is another object of the present invention for the hollow member 12 to be configured so that it can be cleaned and sterilized quickly and easily, thereby reducing, if not eliminating, the risk of cross contamination. In that regard, the hollow member 12 of the present invention is preferably of unitary construction, cast as a single piece, and may therefore be removed from the device 10 for cleaning and sanitizing without the cutting edge 22 existing as a separate piece. In some embodiments, the entirety of the length of the hollow member 12 is a single, polished, smooth surface, both inside and out, which completely lacks any locations where meat may become lodged or ground in during operation. This confers an advantage over other, known devices used for generating samples of meat which have tubular cutting members that come in two pieces and therefore contain areas such as cracks, attachment threading, crevices, or similar areas at the point of connection between the two pieces where meat may become lodged or embedded during operation and which would have to be completely cleaned out after each use in order to effectively remove the risk of cross contamination. Because of the unitary construction and smooth-sided configuration of the hollow member 12, there are no areas where meat may be embedded or ground into during operation of the device 10, which makes cleaning and sterilizing of the hollow member 12 faster and more cost effective, and which also helps ensure that all traces of meat that make contact with the hollow member 12 during operation will be removed during cleaning. This becomes of paramount importance as the device 10 is moved from one location to another for the sampling of meat at a plurality of locations along the meat processing line and across a meat processing plant. In addition, sterilization of the hollow member 12 of the present invention following cleaning has a greater chance of successfully removing any contaminants that may contact the hollow member 12 during operation thereby substantially reducing, if not eliminating, the danger of cross-contamination from one location to another. In contrast, many of the known devices currently existing on the market contain structures such as cracks, attachment threading, crevices and similar areas where meat, together with any contaminants, if present, may become embedded or ground into during operation. If this meat, and any contaminants, are not properly cleaned or removed, they are likely to be transferred to a separate bin, which would then become cross-contaminated and test positive for contaminants where none had previously existed. Further, because these structures are difficult to properly clean and sanitize, when meat becomes embedded or ground into one of these areas in a known device, there is a danger that it may not be removed during cleaning and that any contaminant that may be present in that meat may remain on the known device after cleaning. Any meat remaining in such a structure thus becomes a threat for cross-contamination, even if the device is sterilized subsequent to cleaning. The hollow member 12 of the present invention, being of unitary construction, substantially reduces this risk, if not eliminates it entirely.

In order to remain compliant with the laws and regulations governing the sampling and testing of meat, it will be necessary for meat producers to clean and sanitize the hollow member 12 of the present invention in between uses. Cleaning may occur via any one or more of known processes, from hand washing with soap and water to cleaning with detergents via mechanical and/or electromechanical means. After cleaning, the device 10 is typically sanitized by any one or more of known processes and by the use of any one or combination of known anti-microbial agents, such as treating with chlorinated water, bleach, ozonation, UV-irradiation, and the like. Sanitation ensures that any microbial contaminant remaining after cleaning is destroyed before the next operation of the device 10. In the presently preferred embodiment, the hollow member 12 is completely submergible to facilitate sanitizing after cleaning. The hollow member 12 is preferably made of a material that is incapable of floating on water, such as stainless steel, so that it will sink when placed in sanitizing solutions and make as much contact with the sanitizing solution as possible. This confers an advantage over known devices which typically contain a float, such as a plastic buoy, disposed in the interior of the device that prevents them from sinking. Use of a buoy such as this is disadvantageous as it increases the difficulty of submerging the device under the surface of an appropriate sanitizing solution and therefore increases the risk that sanitation will not be successful. Because the hollow member 12 of the present invention is completely submergible, the speed and effectiveness of the cleaning and sanitizing process is greatly enhanced when compared to these other, known devices. In some embodiments of the present invention, to further assist in cleaning and sanitizing, the interior surface 28 of the hollow member 12 is polished, thereby reducing the coefficient of friction of the interior surface 28 and thus helping to ensure that those pieces of meat that come into contact with the interior surface 28 are easily and completely removed during the cleaning process.

Referring back to FIG. 1, the device 10 includes a driving means 30 that applies rotational motion to the hollow member 12 such that the hollow member 12 rotates about an axis centrally located within the internal cavity 18. The driving means 30 is operably connected to the hollow member 12 via an expelling means 32, which serves to drive the collected samples from the internal cavity 18 of the hollow member 12 after they have been obtained. The presently preferred embodiment for the driving means 30 is a standard hand held power drill with a rotating drill bit that is typically used for drilling holes in various materials, though it is also an object of the present invention that the driving means may be any other hand-held device capable of delivering sufficient rotational motion to the hollow member 12 to enable the hollow member 12 to drill into and through one, and preferably a plurality, of meat pieces. In the preferred embodiment, the drill includes either a 0.5-inch or a ⅜-inch bit (not shown), and is powered by any number of standard means, such as air, electricity, batteries, mechanical manipulation, or other means. The bit is configured to threadingly receive the means for expelling 32, such that the means for expelling 32 is threaded and tightened onto the drill bit prior to operation. In other embodiments, the driving means 30 may be one or more of any other means of applying such rotational motion to the hollow member 12 that is capable of being hand operated by an individual, such as rotary tools, routers or similar devices.

A means for expelling 32 is operably and threadingly connected to the driving means and serves to operably connect the hollow member 12 to the driving means 30. The expelling means 32 also serves to eject the sample(s) from the internal cavity 18 of the hollow member 12 once they have been removed from the meat of interest. Such ejection means may include expulsion via air pressure, physical expulsion such as a plunger, or similar means that may be used to expel a sample of meat from the internal cavity 18 of the hollow member 12 in a sanitary manner. In the presently preferred embodiment, the means for expelling 32 utilizes moderate air pressure to eject the samples from the internal cavity 18 after collection. In this embodiment, the expelling means 32 comprises a housing enclosing a rotatable shank or cylinder (not shown) along with a two-way valved port 38 in a wall of the housing. A proximal end 34 of the expelling means 32 inserts onto the accessory collar of the driving means 30 and the rotatable shank or cylinder threads onto the chuck of the driving means 30 normally. The rotatable shank or cylinder and the chuck of the driving means 30 thus contain threading that is counter to the direction of rotation provided by the driving means 30, so that the expelling means 32 does not loosen during operation but in fact remains tightly connected to the driving means 30. The hollow member 12 connects onto a distal end 36 of the means for expulsion 32, and more specifically to that end of the rotatable shank or cylinder located at the distal end 36 of the expelling means 32. In that regard, that end of the rotatable shank or cylinder located at the distal end 36 of the expelling means 32 includes a chuck (not shown) similar in structure and function to the chuck of the driving means 30, that is operably connected to the rotatable shank or cylinder so that, when the hollow member 12 is connected onto the chuck of the distal end 36, the hollow member 12 is rotated by the driving means 30 simultaneously with the rotatable shank or cylinder of the expelling means 32. In order to accomplish the foregoing, and referring now to FIG. 2 in addition to FIG. 1, the second open end 16 of the hollow member 12 has a coupling mechanism 26 disposed on the interior surface 28 of the hollow member 12 at the second open end 16. This coupling mechanism 26 may be any one or more of many standard means by which two mechanical structures may be operably connected together, such as a clamp, a snap-fit assembly, a bolted or screwed connection, a push-on/turn-on self-locking fastener, a press fit, rivets, and similar means. In the presently preferred embodiment, the coupling mechanism 26 is threading that initiates at the second opening 24 of the hollow member and extends along the interior surface 28 of the hollow member 12 and at least partially into the internal cavity 18. The chuck of that end of the rotatable shank or cylinder located at the distal end 36 of the means for expulsion 32 is threaded in a complimentary fashion so that the hollow member 12 may be threaded thereonto. The chuck of the distal end 36 and the coupling mechanism 26 of the hollow member 12 both contain threading that is counter to the direction of rotation provided by the driving means 30, so that the expelling means 32 and the hollow member 12 do not loosen but in fact remain tightly connected to the driving means 30 during operation.

The two-way valved port 38, located in a wall of the housing of the means for expelling 32, provides the means by which the sample(s) may be ejected from the interior chamber 18 of the hollow member 12 after collection. The port 38 is configured such that it creates a fluid connection between the interior chamber 18 and an external device (not shown) that is capable of providing sufficient force to expel the collected samples from the interior chamber 18. When a valve located inside the port 38 is set in the "off" position, the fluid connection between the interior chamber 18 and the external device is closed and any sample of meat that is present in the interior chamber 18 will remain disposed therein. When this valve is moved to the "on" position, the fluid connection between the interior chamber 18 and the external device is opened and the external device is able to exert sufficient force to drive the sample(s) from the interior chamber intact. There are a number of ways in which the valve may be moved between the "off" and "on" positions by the operator of the device 10, such as a lever, button, switch, shutter, knob, or similar means and the present invention is contemplated for use with any and/or all of such means. Similarly, there are a number of ways in which the device 10 may utilize the fluid connection to expel the sample(s), such as air pressure alone, an air-driven plunger, a mechanical plunger, or similar means. In the presently preferred embodiment, the external device is an air compressor and the means for expulsion 32 employs moderate air pressure to expel the meat sample(s) from the interior chamber 18 when the valve is moved to the "oil" position by the operator of the device 10. In that regard, the presently preferred embodiment for the expulsion means 32 operates in identical fashion to the main body portion of the Air Ejection Corer that is commercially available from J&B Haig Products of Queensland Australia.

Referring now to FIGS. 4A, 4B and 5, a method for using a device 10 made pursuant to at least some embodiments of the present invention is presented. In operation, the device 10 is used to remove at least one sample, and preferably from a plurality of samples, from at least one piece of meat 40, and preferably a plurality of pieces of meat 40, of interest. As shown in FIG. 4A, the meat 40 of interest can be an intact carcass, such that the device 10 is used to drill the hollow member 12 into the carcass in order to remove a single sample 42 therefrom. In the presently preferred embodiment however, as shown in FIG. 4B, the meat 40 is a plurality of production trimmings that are located in a bin 44 capable of holding up to 2,000 pounds of such trimmings, such as those placed in a plurality of locations in a meat processing plant for the purpose of complying with the laws and regulations promulgated for the testing of meat for the presence of microbial contaminants. In that regard, the meat 40 of interest may be any type of production trimmings that may be stored or deposited in such a bin 44, including, without limitation: extra fat beef trimmings, which are mostly fat with trace amounts of lean meat integrated within them; subprimal cuts of a single type or cut of meat that are intended for further processing in preparation for sale to consumers; subprimal cuts of a mixed type that are intended for commercial sale and which will be subjected to a raw, comminuted grind and thereafter sold as ground beef products; and/or any other type of meat product or trimming that may be generated during production and placed in such a bin. In the first step of the inventive process of the present embodiment, the operator picks up the device 10, ensures that the expulsion means 32 is properly attached to the external device and that the valve in the 2-way valved port 38 is configured in the "off" position so that it will not expel the meat 40 sample(s) during operation and ensures that the hollow member 12 is properly attached to that end of the rotatable shank or cylinder located at the distal end 36 of the expelling means 32. The operator then initiates the rotation of the hollow member 12 by turning on the driving means 30 to the desired speed of rotation. Once the desired speed is obtained, the operator contacts the meat 40 with the now rotating cutting surface 22 of the hollow member 12. Thereafter, the operator applies sufficient force to the device 10 to drill the hollow member 12 into the meat 40 to a desired depth; in the case of a plurality of meat 40 pieces, the operator applies sufficient force to drill the hollow member 12 into and through at least one piece of meat 40 and preferably a plurality of meat 40 pieces, thereby obtaining a sample of at least one piece of meat 4, and preferably a plurality of meat 40 pieces, of interest. It is noted that the device 10 of the present invention is capable of drilling the hollow member 12 into the meat 40 an amount equal to, or less than, the length of the hollow member 12, such that any amount of the hollow member 12 may be drilled into the meat 40. The hollow member 12 is configured so that the cutting edge 22, operating under the rotational force of the driving means 30, serves to cut into the meat 40 of interest and to bore into and, if applicable, through the meat 40 under the guidance and pressure delivered by the operator, making a clean cut therethrough. In so doing, the meat 40 is cut so that a sample 42 is cut that matches exactly the size of the interior chamber 18 and which then becomes disposed within the interior chamber 18 of the hollow member 12. A novel aspect to the present invention is that the diameter of the hollow member 12, and thus that of the interior chamber 18, can be sized so that the hollow member 12 cuts and holds one, or a plurality of samples 42 that are of appropriate size for testing for the presence of microbial contaminants. As can be appreciated, if the meat 40 to be sampled is a plurality of production trimmings, the device 10 may be used to drill into, and through, at least one, and preferably a plurality, of such trimmings, thereby taking a sample 42 of each trimming at once, each being the appropriate size for testing. This confers a substantial advantage to the methods previously employed for cutting samples from meat trimmings for microbial testing, in that more than one piece of meat 40 of interest may be sampled at one time, the operator of the device 10 can be ensured that each sample 42 collected is the proper size for testing for the presence of microbial contaminants, and the operator can be ensured that the samples 42 collected will not be damaged or destroyed by the hollow member 12 during collection or expulsion.

The hollow member 12 is adapted to be removed from the meat 40 of interest with the sample(s) 42 obtained from the meat 40 of interest remaining disposed within the internal cavity 18. The hollow member may be so adapted by any number of many means, such as, for example and without limitation, by the presence of one or more annular ridges located along the interior surface 28 that serve to prevent the samples from sliding out of the hollow member 12 but that do not prevent the samples from being expelled by the means for expulsion 32 or from being damaged by such expulsion. In the presently preferred embodiment, the sample(s) 42 are cut to be exactly the same size and shape of the internal cavity 18 and are therefore abutted directly against the interior surface 28 of the hollow member upon collection. The sample(s) 42 are thus tightly packed into the hollow member 12 and will remain disposed within the internal chamber 18 by surface tension during sampling. After the device 10 has been drilled into the meat 40 to the desired depth so as to obtain the desired number of samples 42, the device is withdrawn from the meat 40. The device may be withdrawn with the driving means 30 still in operation, or with the driving means 30 turned off, and the present invention is intended to encompass both such situations, though the driving means 30 should preferably be turned off in advance of expulsion, so as to so increase the likelihood of controlling the trajectory of the sample(s) 42 as they are expelled from the interior chamber 18 hollow member 12. Once the samples(s) 42 are removed from the meat 40 of interest, the sample(s) 42 are expelled from the internal cavity 18 of the device 10 via the expelling means 32, by opening the valve in the two-way valved port 38 as described above. The sample(s) 42 may be expelled into any one of many varying collection articles typically used to handle such sample(s) 42 in an aseptic manner, such as a container or a bag. It is thus an embodiment of the presently preferred embodiment of the present invention to utilize an air pressure with the presently preferred means of expulsion 32 that is sufficiently moderate so as to not damage the collection article in any way when the sample(s) 42 are expelled.

One of many benefits of the present invention is that the device 10 provides a means by which the number of samples 42 collected in each pass, and thus the number of samples collected from each bin 44, is greatly increased over traditional collecting methods, thereby allowing the user to obtain an appropriate number of samples for microbial testing in a fraction of the time traditionally required, which allows the user to collect a greater number of testable samples overall. An increase in the number of samples 42 tested increases the statistical probability of an accurate test result for each bin 44, thereby increasing the probability that the meat producer will be in compliance with the laws and regulations governing the testing and sampling of meat for the presence of microbial contaminants in meat processing plants. Traditionally, an employee of the meat processing plant would hand cut samples 42 from meat 40 trimmings for testing one at a time, and even the best employee would be limited as to the number of samples 42 he or she could collect in a given amount of time, simply because each meat 40 trimming had to be individually cut. The device 10 of the present invention will therefore serve to dramatically increase the number of samples 42 collected by this employee in a single pass, in some cases doubling the number of samples 42 collected and dramatically reducing the number of time required to collect those samples 42.

In one embodiment of the present invention, e.g. see FIG. 2, the hollow core element 23 itself is made of at least one type of material that is flexible and adaptable to being bent in various configurations. For example, in one embodiment, a meat contacting cutting element 22 is provided in association with a flexible plastic hollow tube 22. Also, meat samples when extracted can be immediately packaged in a relatively sterile film 43 to facilitate further analysis of such separated meat, without undue risk of contamination (see FIG. 5).

As shown in FIG. 1, in certain embodiments, plunger-type mechanism 19 is operatively associated with the hollow coring element 18 such that cored meat samples can be expelled from the hollow core center by operation of the plunger 19 to void the collected meat samples from the hollow element 18.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover though the description of the invention has included descriptions of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method of obtaining samples of meat to assay for microbial contamination comprising:
   separating portions of meat from at least three separate animals and combining said portions of meat in a bin adapted to hold up to 2,000 pounds of meat;
   driving, in a single step, a hand-held sampling device into a first, second, and third piece of meat in the bin to obtain a meat core having at least three different animal portions, said meat core having a diameter of between about 0.5 inches to about 3 inches and a length of between about 8 inches and about 16 inches disposed within an internal hollow cavity of an elongated member of said sampling device, said internal hollow cavity comprising a single smooth surface lacking any removable portion along the length of the elongated member, and said internal hollow cavity having a first opening having a cutting surface formed around an entire circumference of a first end of said elongated member, and said internal hollow cavity having a second end comprising a threaded coupling mechanism, said elongated member threadably engaging said hand-held sampling device;
   removing said sampling device from said bin with said core of meat having at least three different animal portions remaining disposed within said hollow cavity;
   expelling said core of meat from said hollow cavity through said first end to obtain said core meat sample of a size, length, and diameter suitable for assaying said meat core for microbial contamination; and
   wherein said first end of said elongated member further includes a flexible plastic hollow tube.

2. The method of claim 1, wherein said portions of meat are from a bovine.

3. The method of claim 1, wherein said driving step includes rotating said elongated member of said sampling device.

4. The method of claim 1, wherein said driving step comprises driving said sampling device into more than 3 distinct portions of meat in a single driving step.

5. The method of claim 1, further comprising, prior to said driving step, sanitizing said sampling device by employing a sanitization procedure selected from the group consisting of: washing with soap and water, detergents, anti-microbial agents, chlorinated water, bleach, ozonation, and UV-irradiation.

6. The method of claim 1, wherein said expelling step includes employing an air-driven plunger.

7. The method of claim 1, wherein said threaded coupling mechanism includes threading on said second end of said elongated member being counter to a direction of rotation of said elongated member.

8. The method of claim 1, wherein said driving step includes applying sufficient force to said sampling device to drill said elongated member to a desired depth.

9. The method of claim 1, further comprising providing a plunger mechanism operatively associated with said elongated member to expel said meat core by operation of said plunger to void said meat core from said hollow cavity.

10. A method of obtaining samples of meat to assay for microbial contamination, comprising:
    separating portions of meat from at least three separate animals and combining said portions of meat in a bin adapted to hold up to 2,000 pounds of meat;
    driving, in a single step, a hand-held sampling device into a first, second, and third piece of meat in the bin to obtain a meat core having at least three different animal portions, said meat core having a diameter of between about 0.5 inches to about 3 inches and a length of between about 8 inches and about 16 inches disposed within an internal hollow cavity of an elongated member of said sampling device, said internal hollow cavity comprising a single smooth surface lacking any removable portion along the length of the elongated member, and said internal hollow cavity having a first opening having a cutting surface formed around an entire circumference of a first end of said elongated member, and said internal hollow cavity having a second end comprising a threaded coupling mechanism, said elongated member threadably engaging said hand-held sampling device;

removing said sampling device from said bin with said core of meat having at least three different animal portions remaining disposed within said hollow cavity;

expelling said core of meat from said hollow cavity through said first end to obtain said core meat sample of a size, length, and diameter suitable for assaying said meat core for microbial contamination; and wherein said meat core is expelled into a plastic film disposed inside said elongated member such that when said meat core is expelled, said meat core is packaged in a said plastic film.

11. The method of claim 10, wherein said portions of meat are from a bovine.

12. The method of claim 10, wherein said driving step includes rotating said elongated member of said sampling device.

13. The method of claim 10, further comprising, prior to said driving step, sanitizing said sampling device by employing a sanitization procedure selected from the group consisting of: washing with soap and water, detergents, anti-microbial agents, chlorinated water, bleach, ozonation, and UV-irradiation.

14. The method of claim 10, wherein said expelling step includes employing an air-driven plunger.

15. The method of claim 10, wherein said threaded coupling mechanism includes threading on said second end of said elongated member being counter to a direction of rotation of said elongated member.

16. The method of claim 10, wherein said driving step includes applying sufficient force to said sampling device to drill said elongated member to a desired depth.

17. The method of claim 10, further comprising providing a plunger mechanism operatively associated, with said elongated member to expel said meat core by operation of said plunger to void said meat core from said hollow cavity.

18. The method of claim 10, wherein said driving step comprises driving said sampling device into more than three distinct portions of meat in a single driving step.

* * * * *